(12) United States Patent
Sims et al.

(10) Patent No.: US 7,867,197 B2
(45) Date of Patent: Jan. 11, 2011

(54) SINGLE-DOSE SYRINGE DRIVER

(75) Inventors: Nathaniel M. Sims, Milton, MA (US); Michael H. Wollowitz, Chatham, NY (US)

(73) Assignee: The General Hospital Corporation, Boston, MA (US)

( * ) Notice: Subject to any disclaimer, the term of this patent is extended or adjusted under 35 U.S.C. 154(b) by 546 days.

(21) Appl. No.: 11/277,848

(22) Filed: Mar. 29, 2006

(65) Prior Publication Data

US 2007/0233004 A1 Oct. 4, 2007

(51) Int. Cl.
*A61M 5/20* (2006.01)
(52) U.S. Cl. ..................... 604/134; 601/131
(58) Field of Classification Search ......... 604/151–155, 604/533–535, 538, 131–135; 128/DIG. 12
See application file for complete search history.

(56) References Cited

U.S. PATENT DOCUMENTS

| | | | |
|---|---|---|---|
| 2,632,445 A | 3/1953 | Kas, Sr. | |
| 4,059,110 A | 11/1977 | Wuthrich et al. | |
| 4,132,231 A | 1/1979 | Puccio | |
| 4,202,333 A | 5/1980 | Thill et al. | |
| 4,298,000 A * | 11/1981 | Thill et al. | 604/135 |
| 4,381,006 A * | 4/1983 | Genese | 604/135 |
| 4,430,079 A | 2/1984 | Thill et al. | |
| 4,465,478 A | 8/1984 | Sabelman et al. | |
| 4,498,904 A | 2/1985 | Turner et al. | |
| 4,544,369 A | 10/1985 | Skakoon et al. | |
| 4,547,189 A | 10/1985 | Moore et al. | |
| 4,597,754 A | 7/1986 | Thill et al. | |
| 4,608,042 A * | 8/1986 | Vanderveen et al. | 604/81 |
| 4,636,197 A * | 1/1987 | Chu | 604/131 |
| 4,652,260 A * | 3/1987 | Fenton et al. | 604/67 |
| 4,676,122 A | 6/1987 | Szabo et al. | |
| 4,804,368 A | 2/1989 | Skakoon et al. | |
| 4,943,279 A | 7/1990 | Samiotes et al. | |
| 5,004,124 A | 4/1991 | Stefaniak et al. | |
| 5,092,842 A | 3/1992 | Bechtold et al. | |
| 5,140,862 A | 8/1992 | Pappalardo | |
| 5,176,646 A | 1/1993 | Kuroda | |
| 5,232,459 A | 8/1993 | Hjertman | |
| 5,300,041 A | 4/1994 | Haber et al. | |
| 5,318,539 A | 6/1994 | O'Neil | |
| 5,328,486 A | 7/1994 | Woodruff | |
| 5,429,607 A | 7/1995 | McPhee | |
| 5,599,315 A | 2/1997 | McPhee | |
| 5,722,956 A * | 3/1998 | Sims et al. | 604/131 |
| 5,954,695 A | 9/1999 | Sims et al. | |

OTHER PUBLICATIONS

Product Brochure "Freedom60 Syringe Infusion System" Repro-Med Systems, Inc., 1998.

* cited by examiner

*Primary Examiner*—Kevin C Sirmons
*Assistant Examiner*—Laura C Schell
(74) *Attorney, Agent, or Firm*—Nutter McClennen & Fish LLP

(57) ABSTRACT

Various methods and devices for driving fluid from a syringe are provided. In one exemplary embodiment, a syringe driver is provided having a frame that is adapted to seat a syringe, a driver that is slidably disposed within the frame and that is adapted to seat a plunger of a syringe, and a puller that is slidably disposed within the frame and that has a latch formed thereon for mating to an engagement element on the frame. The device can also include a force-delivery element, such as a constant force spring, that is coupled to and extends between the driver and the puller. In use, the puller is movable between a first position, in which the force-delivery element is in a resting position, and a second position, in which the latch on the puller mates to the engagement element on the frame to expand the force-delivery element thereby causing the force-delivery element to pull the driver and drive a plunger into a barrel of a syringe seated within the frame to deliver fluid from the syringe to a patient at a constant rate.

47 Claims, 16 Drawing Sheets

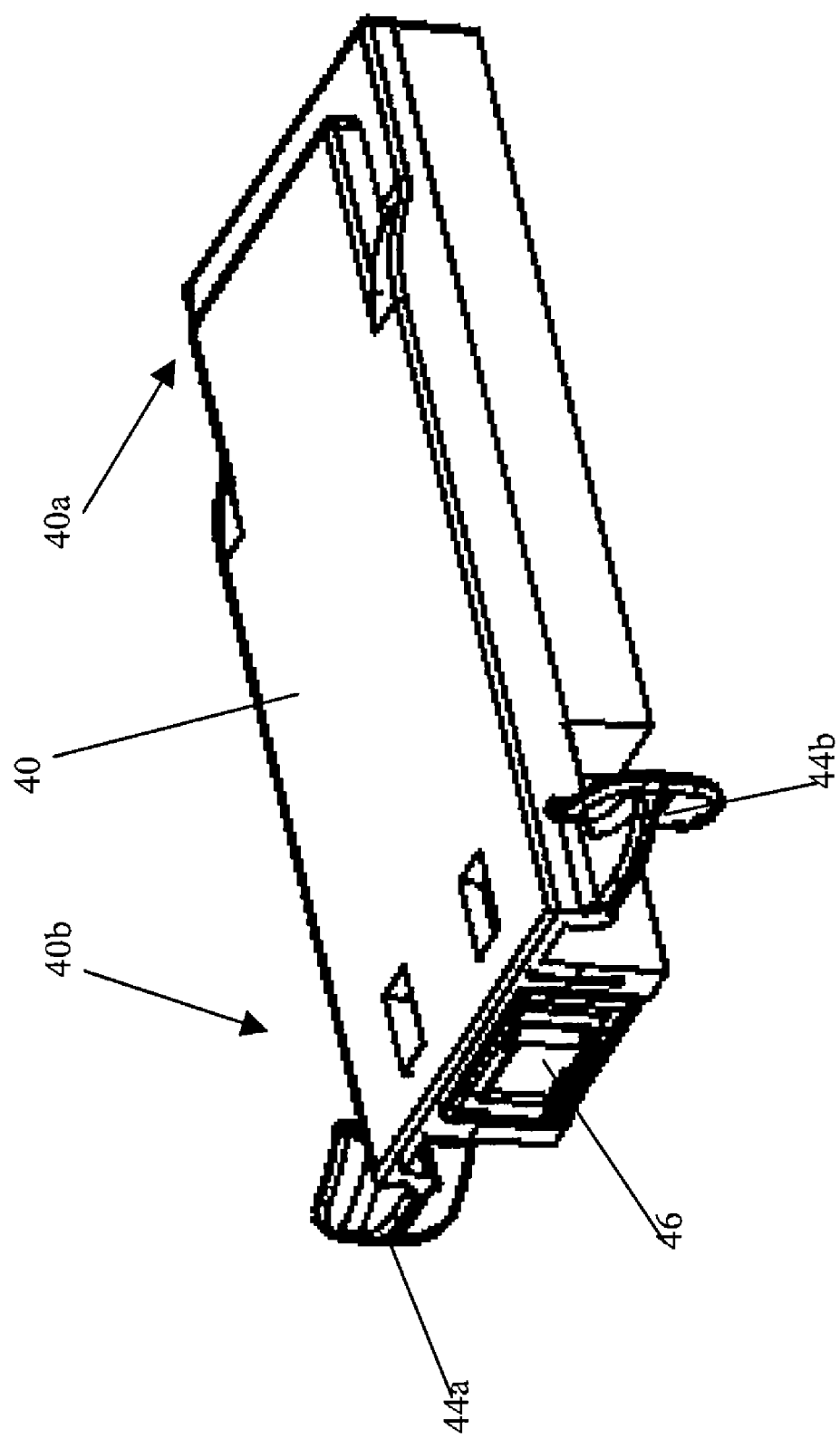

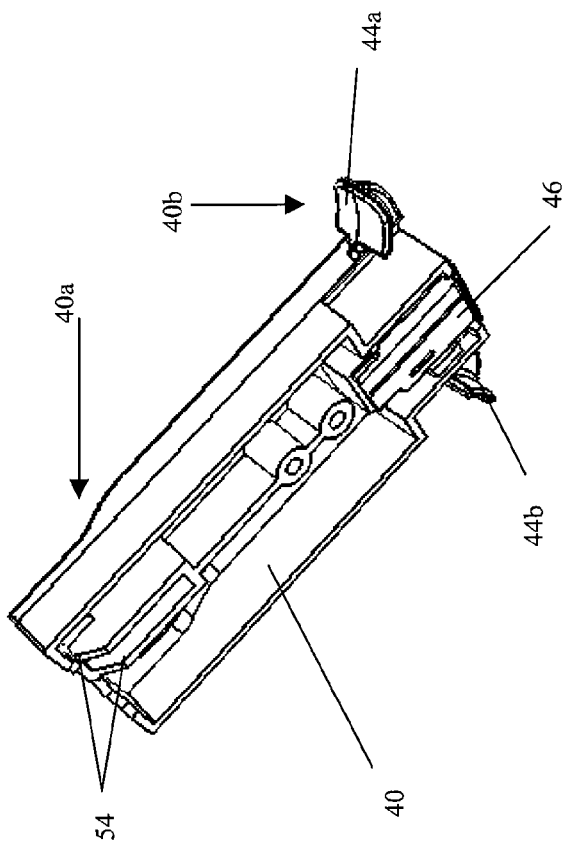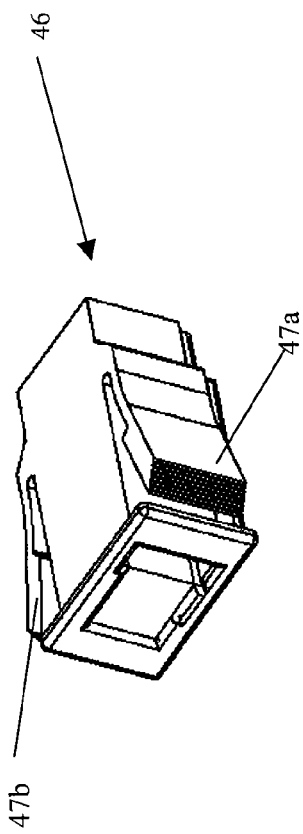

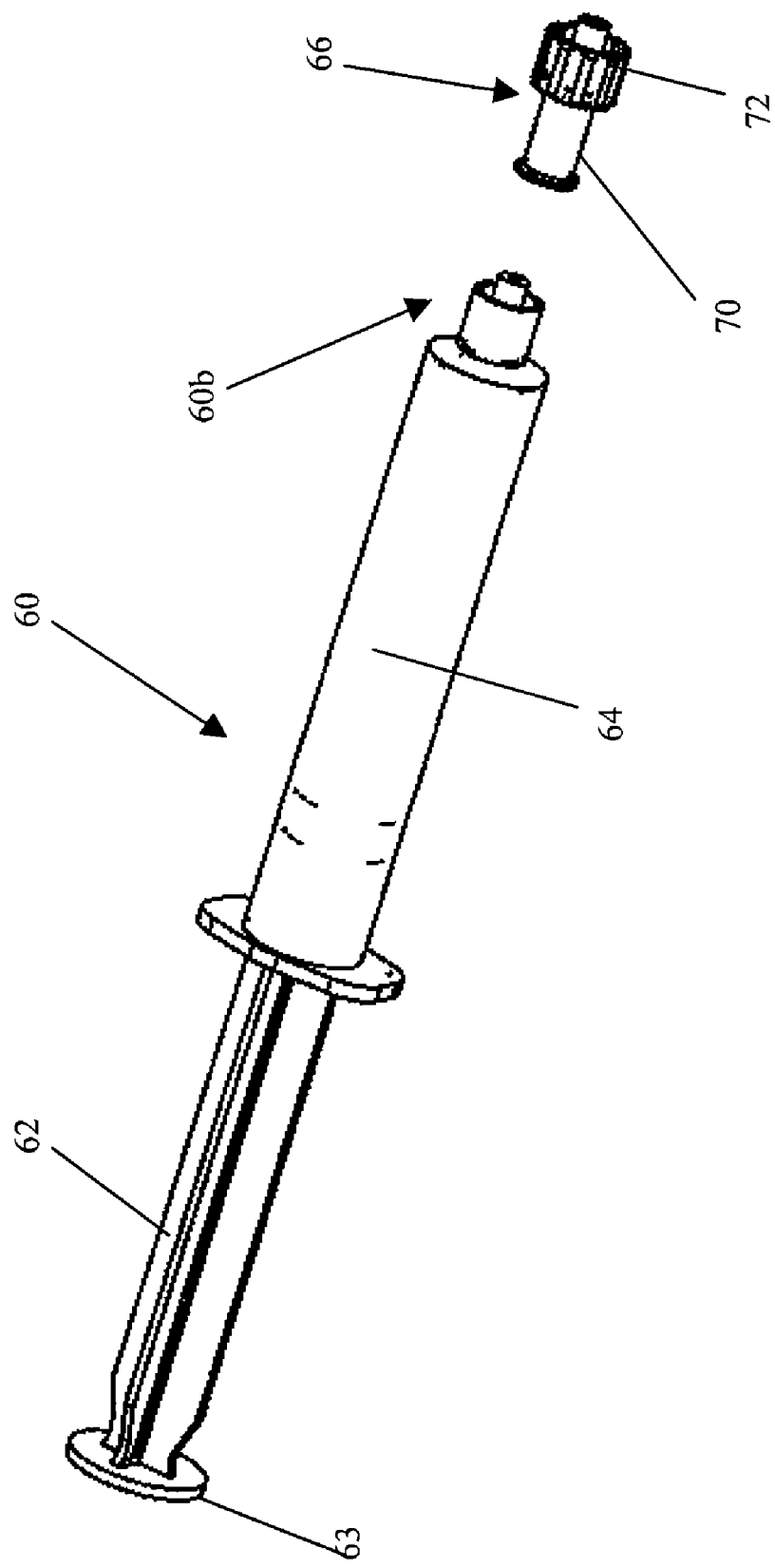

SINGLE-DOSE SYRINGE DRIVER

FIELD OF THE INVENTION

The present invention relates to devices and methods for driving fluid from a syringe.

BACKGROUND OF THE INVENTION

Certain medical fluids are administered by controlled infusion and require a slow but non-rate critical flow rate. Infusion of a medical fluid in this manner has generally been accomplished by use of a drip bag gravity-feed system or an electronic infusion pump. The drip bag provides a non-rate critical flow with a simple and relatively inexpensive apparatus. However, in certain applications, particularly those involving small fluid volumes, the use of disposable syringes is preferred to drip bags. Administration of medical fluids at a low flow rate using a syringe is generally accomplished by the use of a predetermined force that is applied to the syringe plunger so that fluid resistance acts to control the flow rate. Current devices for applying force to a syringe plunger can have a housing for holding the syringe and a simple mechanism located within the housing that causes force to be applied to the plunger. While effective, these devices are often designed to be used with proprietary syringe sets, rendering medical fluid administration expensive.

Accordingly, there remains a need for an improved syringe driver, and in particular for a syringe driver that can be used with standard medical syringes.

SUMMARY OF THE INVENTION

The present invention provides various devices and methods for driving fluid from a syringe. In one embodiment, a syringe driver is provided having a frame that is adapted to seat a syringe, a driver that is slidably disposed within the frame and that is adapted to seat a plunger of a syringe, and a puller that is slidably disposed within the frame. The device can also include a force-delivery element, such as a constant force spring, that is coupled to and extends between the driver and the puller. In use, the puller is movable between a first position, in which the force-delivery element is in a resting position, and a second position, in which the puller mates to the frame to expand the force-delivery element thereby causing the force-delivery element to pull the driver and drive a plunger into a barrel of a syringe seated within the frame.

A variety of techniques can be used to mate a syringe to the device, but in one exemplary embodiment the driver includes a cavity formed therein and adapted to capture a flange formed on a proximal end of a plunger of a syringe, and the frame includes a connecting element formed on a distal end thereof and adapted to connect to a distal end of a syringe. The connecting element can include, for example, a cavity that is adapted to receive a barrel of the syringe and a protrusion that is adapted to receive at least a portion of a detachable luer fitting for mating to a distal end of the barrel of the syringe. The detachable luer fitting can be configured to mate to any standard syringe, thereby allowing the device to interchangeably receive syringes having various sizes. In one embodiment, the luer fitting can have a non-threaded socket formed therein for receiving the protrusion formed on the connection element.

The driver, puller, and force-delivery element can also have a variety of configurations, and they can be coupled to the frame using a variety of techniques. In one exemplary embodiment, the frame can include a proximal portion for slidably seating the driver therein, and a distal portion for slidably seating the puller. The frame can optionally include rails formed thereon for slidably retaining the driver within the frame, and a housing that at least partially surrounds the puller to retain the puller within the frame. In certain exemplary embodiments, the force-delivery element can be adapted to force the puller into contact with the housing to generate friction between the puller and the housing when the puller is in the first position, and thereby help retain the puller in the first position. The driver can also include a first engagement surface formed thereon and adapted to act against a second, complementary engagement surface formed on the puller to further force the puller into contact with the housing to generate a friction between the housing and the puller when the puller is in the first position. The engagement surfaces can be, for example, complementary ramp elements.

As indicated above, the puller is preferably adapted to mate to a distal end of the frame to actuate the force-delivery element, and thereby move the driver to advance a plunger into a syringe held within the frame. While various techniques can be used to mate the puller to the distal end of the frame, in one embodiment the puller can include a latch formed on a distal end thereof, and the frame can include an engagement element formed on a distal end thereof. The puller can optionally include one or more handles formed thereon for slidably moving the puller to mate the latch to the engagement element. The latch and engagement element can be releasably matable, and depression of the handle(s) can be adapted to release the latch from the engagement element.

A system for driving fluid is also provided and includes a syringe having a barrel and a plunger slidably disposed in the barrel, and a syringe driver having a frame with a proximal end and a distal end that is adapted to couple to a distal end of the barrel of the syringe. A driver is slidably disposed within the frame and is adapted to retain a proximal end of the plunger. A puller is slidably disposed within the frame and is movable between a first position, in which the puller is positioned adjacent to the driver, and a second position, in which the puller is coupled to a distal end of the frame and a force is applied to the driver to move the driver distally, and thereby force the plunger into the barrel of the syringe. The syringe driver can also include a force-delivery element extending between the puller and the driver. The force-delivery element can be in a resting position when the puller is in the first position, and the force-delivery element can be actuated to apply a force to the driver when the puller is in the second position.

In another embodiment, a system for driving fluid can include a syringe having a barrel, a plunger slidably disposed in the barrel, and a luer fitting coupled to a distal end of the barrel for mating the barrel to a fluid conduit. The system can also include a frame having proximal and distal ends, the proximal end adapted to retain the plunger and the distal end having a connecting element formed thereon adapted to couple to the barrel of the syringe. The connecting element can include a protrusion that is configured to extend into a non-threaded socket formed in the luer fitting to removably mate the barrel to the frame.

Methods for driving fluid are also provided. In one exemplary embodiment, the method can include engaging a syringe between a driver slidably positioned within a frame and a connecting element formed on a distal end of the frame, and sliding a puller toward a distal end of the frame to mate the puller to the frame. Sliding the puller will actuate a force-delivery element coupled to and extending between the puller and the driver. Once actuated, the force-delivery element will move the driver distally to drive a plunger into a barrel of the syringe and thereby drive fluid out of the syringe. In an exemplary embodiment, the puller can be slid by sliding opposed handles formed on the puller distally within opposed slots formed in the housing. Depressing the opposed handles can be effective to release the puller from the frame. In another exemplary embodiment, engaging the syringe can include positioning a flange formed on a proximal end of a plunger of the syringe in a cavity formed in the driver, and positioning a luer fitting coupled to a distal end of the syringe within a protrusion formed on the connecting element.

BRIEF DESCRIPTION OF THE DRAWINGS

The invention will be more fully understood from the following detailed description taken in conjunction with the accompanying drawings, in which:

FIG. 5A is a top perspective view of a puller of the syringe driver of FIG. 1;

FIG. 5B is a bottom perspective view of the puller of FIG. 5A;

FIG. 5C is a perspective view of a latch on the distal end of the puller of FIG. 5A;

FIG. 7 is a partially exploded view of the syringe and a luer fitting of the system of FIG. 1;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
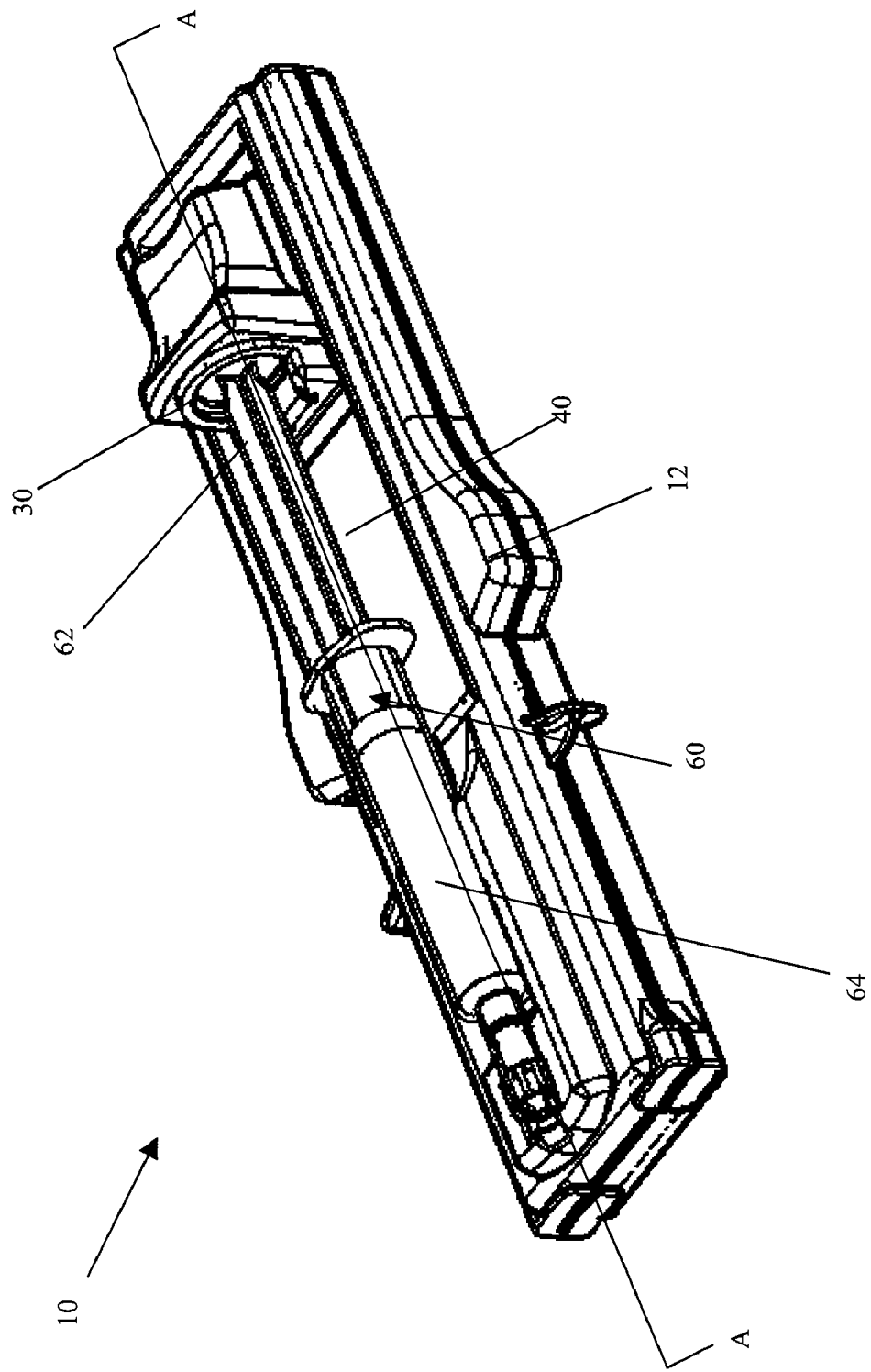
FIG. 1 is a perspective view of one embodiment of a syringe and a syringe driver for driving fluid from a syringe.

The present invention generally provides devices and methods for driving fluid from a syringe. In general, the system includes a syringe that can be mated to a syringe driver to cause fluid to be driven from the syringe, preferably at a constant rate. FIG. 1 illustrates one exemplary embodiment of a device for driving fluid from a syringe. As shown, the device 10 includes a frame 12 that is adapted to seat a syringe 60, a driver 30 slidably disposed within the frame 12 and adapted to apply a driving force to the syringe 60, and a puller 40 slidably disposed within the frame 12 and adapted to move the driver 30 relative to the frame 12. The device 10 can also include a force-delivery element (not shown) coupled to and extending between the driver 30 and the puller 40. In use, the puller 40 can be moved from an initial position to an actuated position to actuate the force delivery element. As a result, the force-delivery element will force the driver 30 distally to move a plunger 62 of the syringe 60 into a barrel 64 of the syringe 60, thereby forcing fluid out of the syringe 60. The system is particularly effective for delivering medical fluids such as antibiotics, chemotherapy agents, and other drugs typically handled in IV bags, however the syringe can be used to deliver any fluid.

Figure 2A:
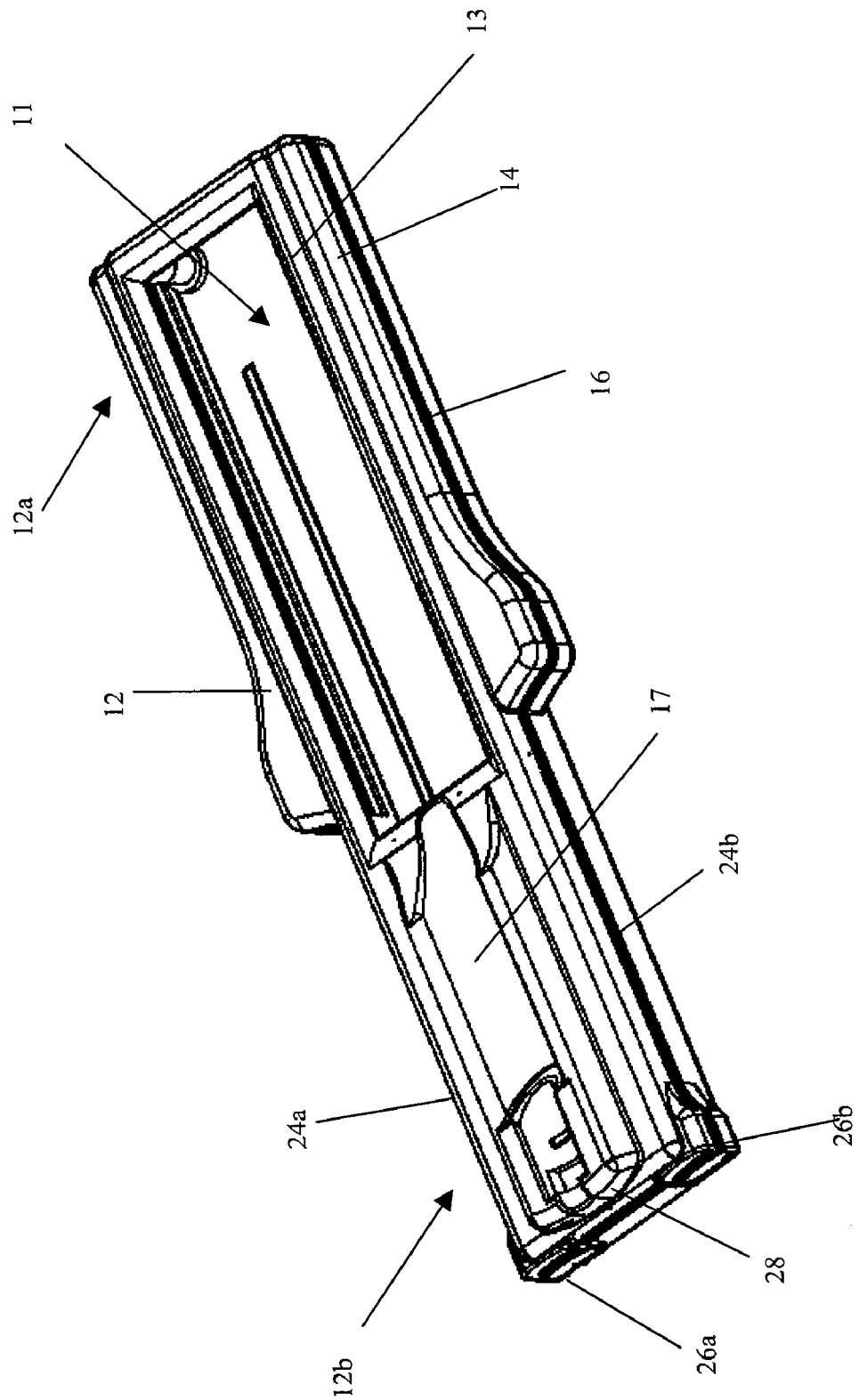
FIG. 2A is a perspective view of a frame of the syringe driver of FIG. 1.
Figure 2B:
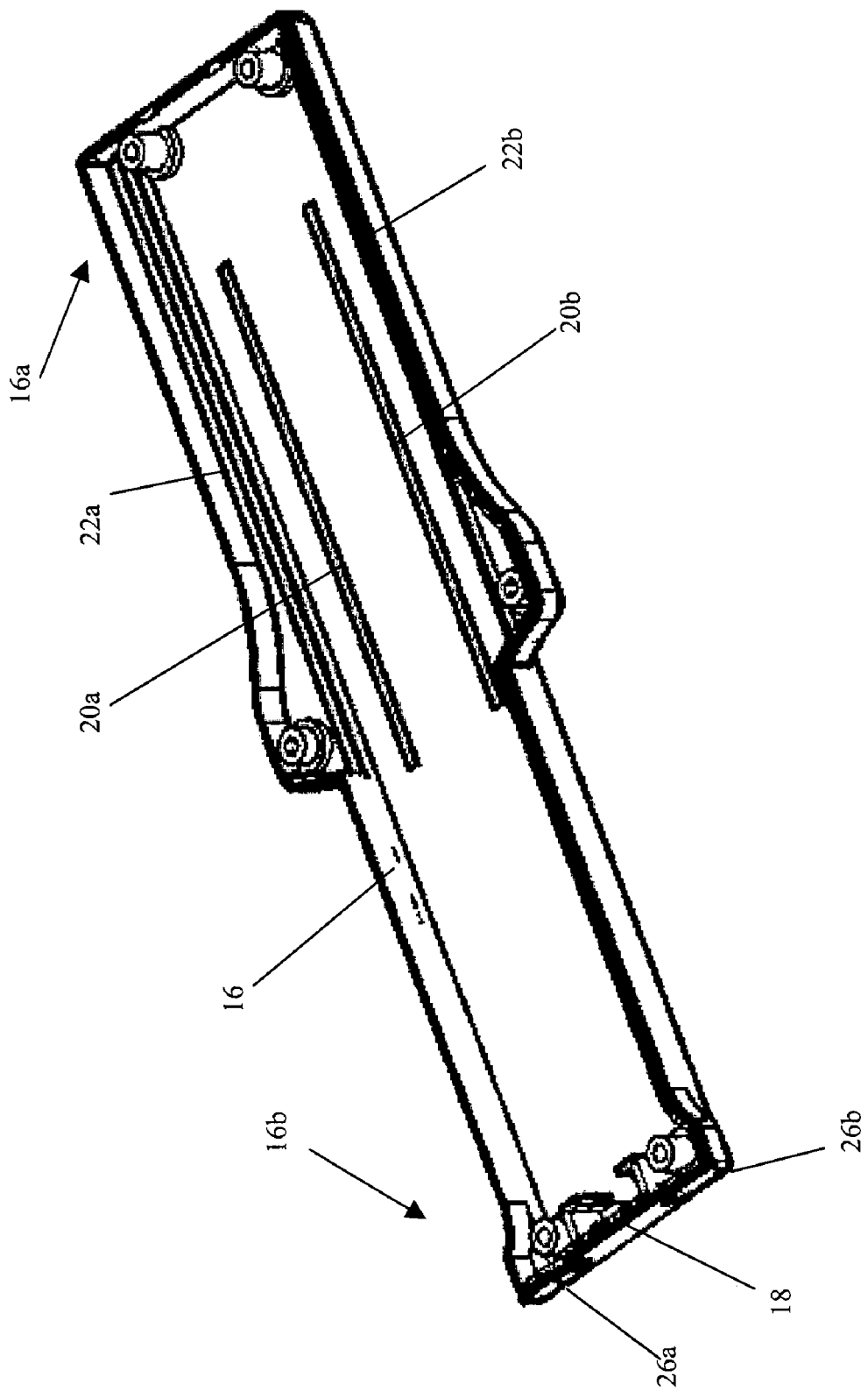
FIG. 2B is a perspective view of the bottom portion of the frame of FIG. 2A.
Figure 2C:
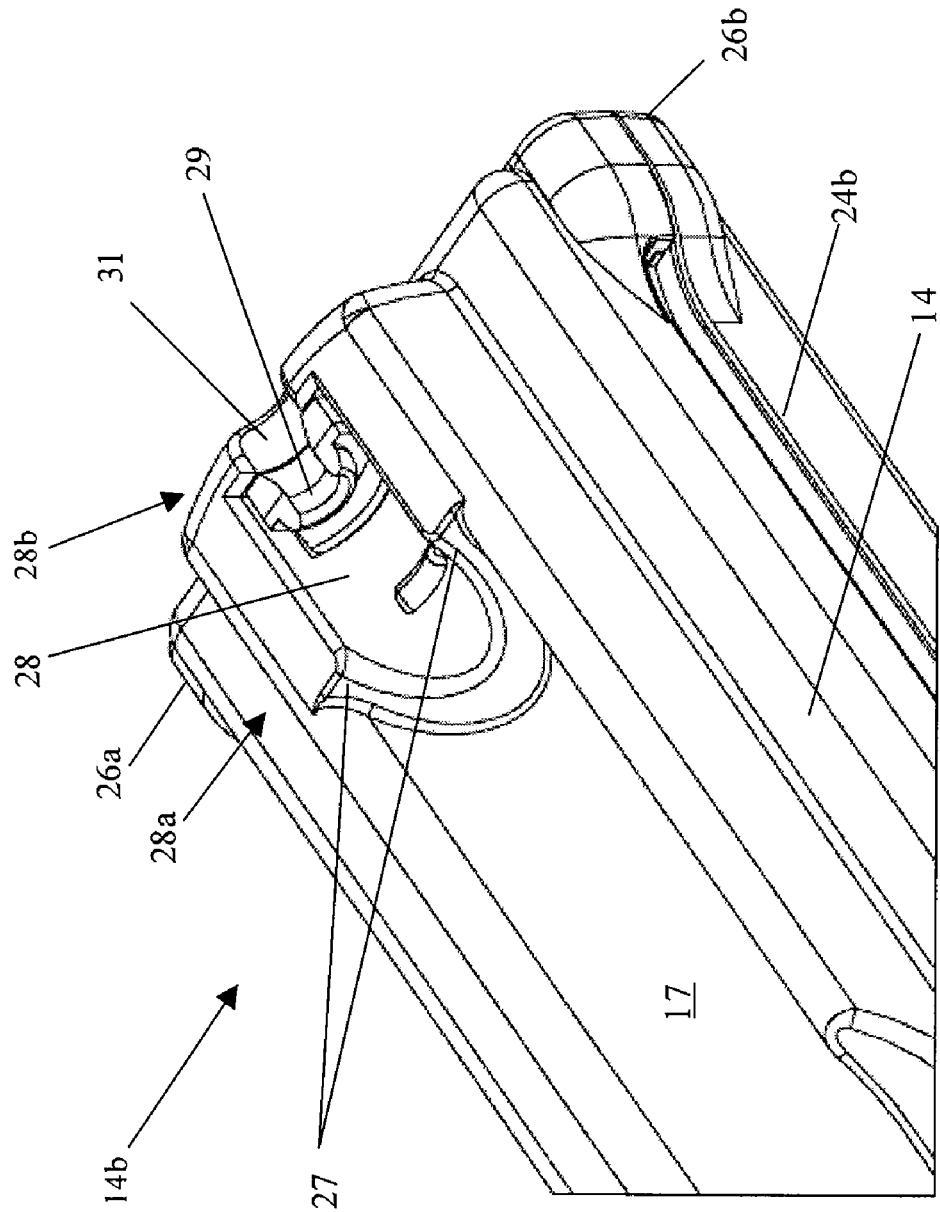
FIG. 2C is an enlarged perspective view of a connecting element for receiving a syringe located on the distal end of the frame of FIG. 2A.

FIGS. 2A-2C illustrate the frame 12 of the syringe driver 10 in more detail. While the frame 12 can have any shape, size, and configuration, in the embodiment shown in FIG. 2A the frame 12 is in the form of a substantially rectangular-shaped housing with proximal and distal ends 12a, 12b. The frame 12 can have a unitary configuration, or it can include a top and bottom portion 14, 16 that mate together. A two-piece configuration is advantageous as the top and bottom portions 14, 16 can seat the driver 30, puller 40, and force-delivery element therebetween, and the top portion 14 can be adapted to hold the syringe. The frame 12 can also optionally include features to facilitate grasping of the puller 40 and use of the device 10. As shown in FIG. 2A, the frame 12 includes two protrusions 26a, 26b formed on opposed sidewalls thereof to receive the thumbs of a user to facilitate movement of the puller 40, as will be discussed in more detail below. The frame 12 can also include mounting features integrally formed thereon or coupled thereto that allow the device 10 to be hung from a rack or mounted to a vertical or horizontal surface depending upon the needs of the user. Exemplary mounting features include, for example, hooks, one or more bores or screw holes for receiving a fastener, adhesive, etc.

As noted above, the driver 30 and the puller 40 can be slidably disposed within the frame 12. While various techniques can be used to slidably couple the driver 30 and the puller 40 to the frame 12, in the embodiment shown in FIG. 2B the bottom portion 16 of the frame 12 includes a first set of tracks or rails 20a, 20b formed on a bottom wall thereof for seating the driver 30, and a second set of tracks or rails 22a, 22b formed on opposed sidewalls thereof for seating the puller 40. The frame 12 can also include features that allow a user to slide the puller 40 within the tracks 22a, 22b such that the puller 40 can be moved from a first position to a second position to cause movement of the force-delivery element. For example, referring back to FIG. 2A, the top and bottom portions 14, 16 of the frame 12 can include slots 24a, 24b that are adapted to receive handles 44a, 44b located on the puller 40. Movement of the handles 44a, 44b within the slots 24a, 24b can actuate the puller 40 to thereby actuate the force-delivery element, as will be discussed below.

The top portion 14 of the frame 12 can be adapted to receive a syringe. While the frame 12 can have various features for seating a syringe, FIG. 2A illustrates a semi-cylindrical cavity 17 formed thereon for seating a barrel of the syringe. A plunger on the syringe can couple to the driver 30, as will be discussed below, and a distal end of the syringe can couple to the frame 12. While various mating techniques can be used, in an exemplary embodiment the top portion 14 of the frame 12 includes a connecting element formed thereon having a cavity 28 for seating a connector that couples to a distal end of the syringe to hold and support the syringe within the cavity 17 of the frame 12. The cavity 28 can have any shape and size, and the configuration of the cavity 28 can vary depending upon the connector used. However, in an exemplary embodiment the connector is in the form of a luer fitting that can be used with any size syringe, and the cavity 28 is in the form of a semi-circle with proximal and distal ends 28a, 28b. An exemplary luer fitting will be discussed in more detail below with respect to FIGS. 7 and 10. The connecting element can also include features to prevent inadvertent engagement with the wrong type of fitting, such as rounded corners 27. In an exemplary embodiment, the distal end 28b of the cavity 28 includes a protrusion 29 extending therefrom and adapted to extend into and mate with the luer fitting. The protrusion 29 can have various shapes and sizes. As shown in FIG. 2C, the protrusion 29 is semi-circular. The protrusion 29 can also include features, such as a cut-out 31, for seating a fluid conduit, such as tubing, for carrying fluid that extends from the luer fitting. The connecting element can be formed integrally with the frame 12 or separate therefrom. In one embodiment, the connecting element is separate from the frame 12 and can be slid into a slot (not shown) located on the distal end 14b of the top portion 14. This allows the connecting element to be replaced should the protrusion 29 break as a result of stress from the weight of the syringe.

A person skilled in the art will appreciate that the frame 12 can have a variety of other configurations and it can include a variety of other features known in the art. For example, as shown in FIG. 2A, the top portion 14 can include a cut-out 11 formed therein for receiving the driver 30 therethrough. As a result, the top portion 14 can include a flange 13 that can be located around the cut-out 11 to retain the driver 30 and the puller 40 within the frame 12.

Figure 3A:
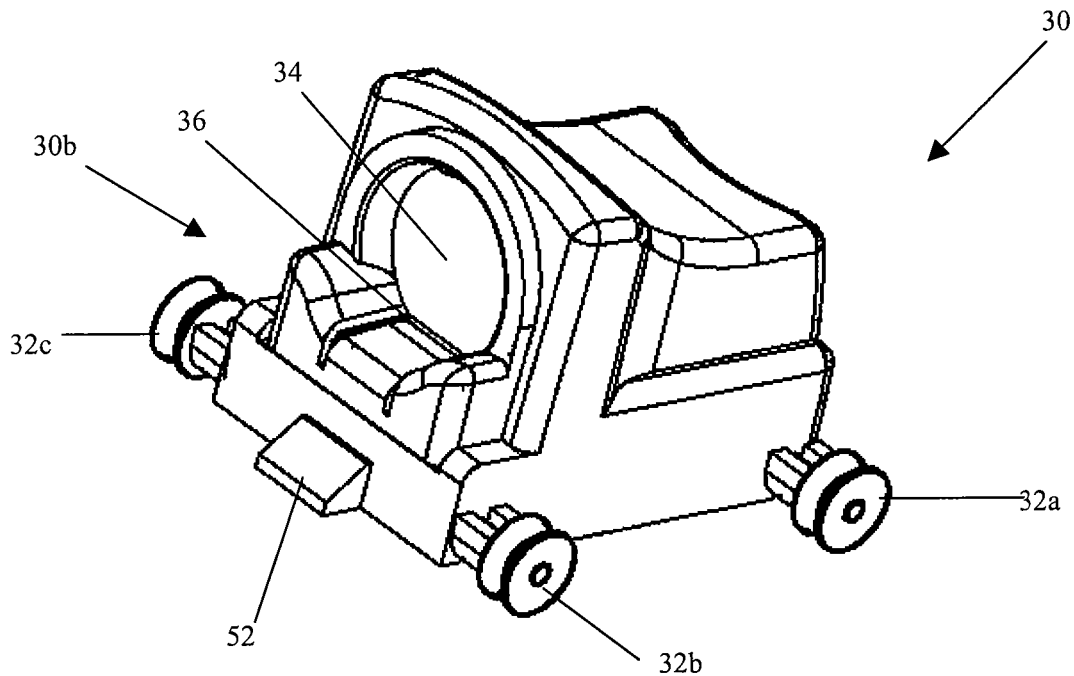
FIG. 3A is a top perspective view of a driver of the syringe driver of FIG. 1.
Figure 3B:
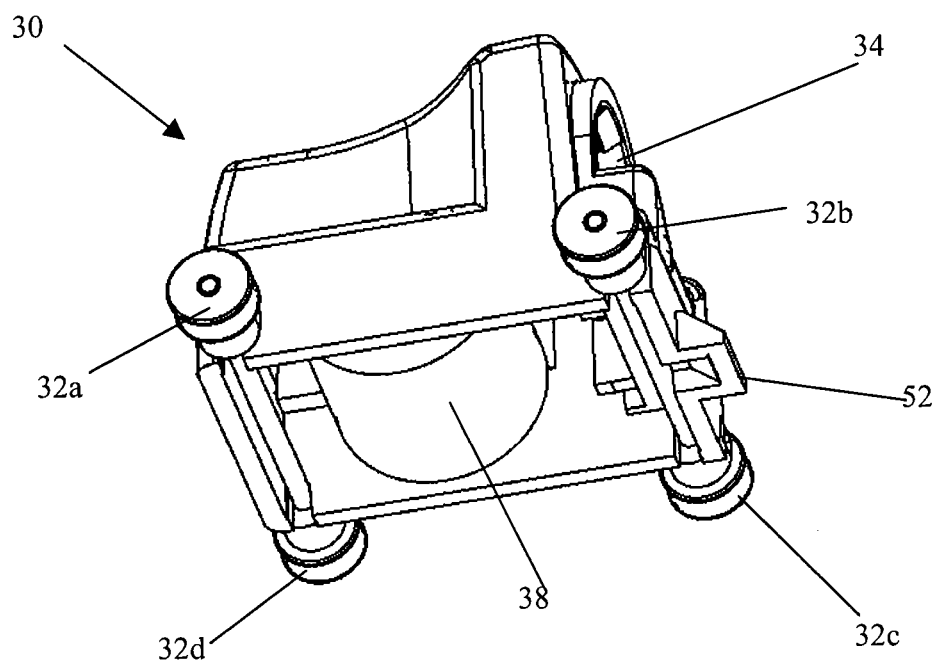
FIG. 3B is a bottom perspective view of the driver of FIG. 3A.
Figure 4:
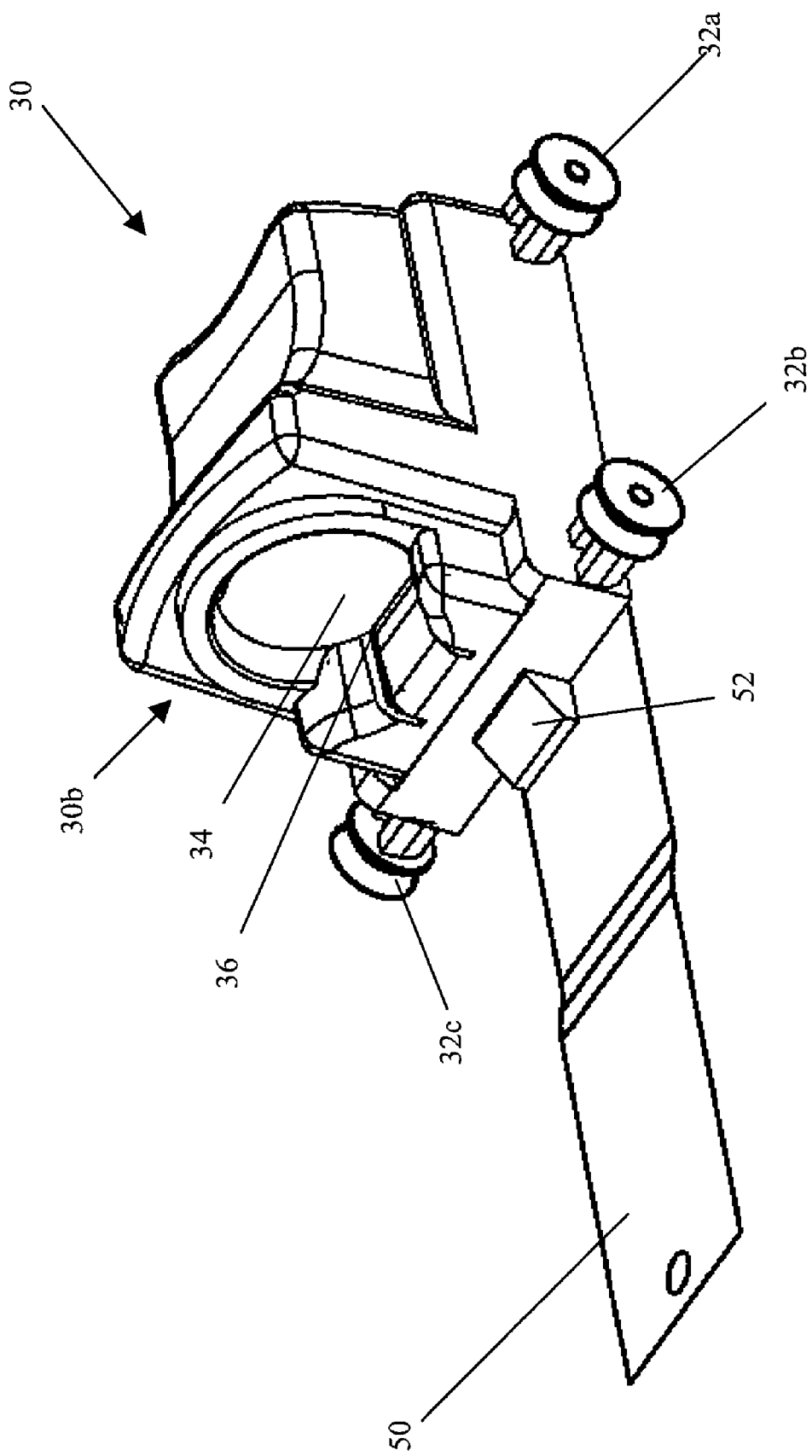
FIG. 4 is a perspective view of a force-delivery element and the driver of FIG. 1.
Figure 6:
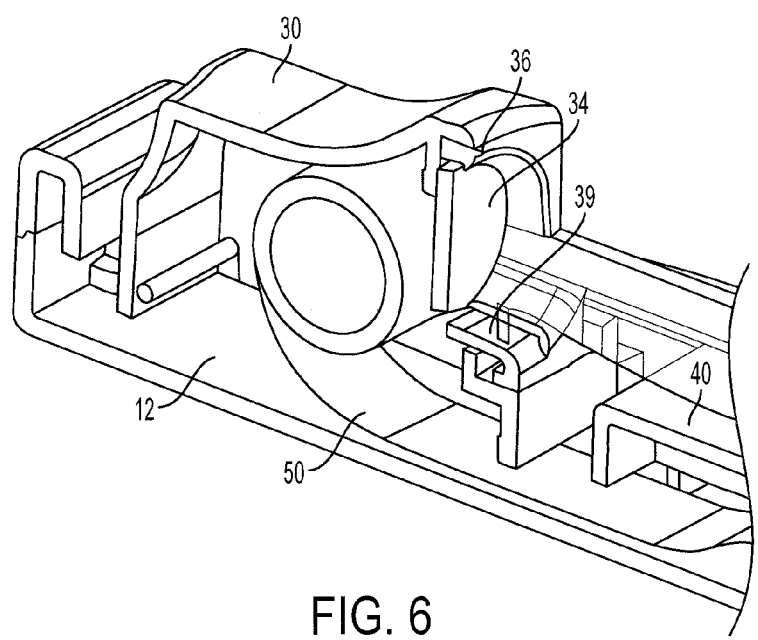
FIG. 6 is a cross-sectional view of a proximal portion of the syringe driver of FIG. 1 taken across line A-A.

The driver 30 is shown in more detail in FIGS. 3A-4, and while it can have a variety of shapes and sizes, in an exemplary embodiment the driver 30 is in the form of a housing that is adapted to hold a force-delivery element, as will be discussed below. As previously discussed, the driver 30 can be slidably disposed within the frame 12. To facilitate sliding, the driver 30 can include wheels 32a, 32b, 32c, 32d that are located on opposed sides of the housing and that are adapted to sit within the tracks 20a, 20b in the bottom wall of the frame 12 (shown in FIG. 2B). The driver 30 can also be adapted to seat a portion of the syringe, and thus the distal end 30b of the driver 30 can include a cavity 34 or other feature formed therein for receiving the plunger of a syringe or other device for advancing a plunger into a syringe. While the cavity 34 can merely be molded within the driver 30, it can alternatively be adapted to facilitate engagement with the plunger. For example, the driver 30 can include a latch 36 formed thereon and configured to engage a flange formed on the proximal end of the plunger of the syringe. The driver 30 can also include a spring-loaded backwall (spring 39 is shown in FIG. 6) to facilitate insertion and removal of the plunger from the cavity 34. In use, when the syringe is coupled to the driver 30, the driver 30 can slide within the cut-out 11 of the frame 12 to cause the plunger to be driven into the barrel of the syringe.

As previously indicated, the device 10 can also include a force-delivery element coupled between the driver 30 and the puller 40 that can be used to apply a force to the driver 30 to cause the driver 30 to drive a plunger into a barrel of a syringe seated within the device 10. While various force-delivery mechanisms can be used, in an exemplary embodiment, the force-delivery element is a constant force spring 50 (as shown in FIG. 4) that is wound around and mated to a hub 38 formed within the driver 30, and that includes a free end that is mated to the puller 40. In use, movement of the puller 40 will extend the force-delivery element 50 to an expanded or unwound position. As a result, the force-delivery element 50 will pull the driver 30 distally thereby causing the plunger to be driven into the barrel of the syringe, as will be discussed in more detail below. While the illustrated driver 30 includes a hub 38 for mating to the force-delivery element 50, a person skilled in the art will appreciate that a variety of other techniques can be used to couple the driver 30 and the puller 40.

The puller 40 is shown in more detail in FIGS. 5A-5C. While the puller 40 can have a variety of configurations, FIGS. 5A-5C illustrate a substantially rectangular puller 40 having proximal and distal ends 40a, 40b. The puller 40 can include rails, wheels, or some other mechanism (not shown) located on opposed sides thereof to facilitate sliding within the tracks 22a, 22b in the sidewalls of the frame 12 (shown in FIG. 2B). The puller 40 can also include handles 44a, 44b located on opposed sides thereof to facilitate movement of the puller 40 within the frame 12. In an exemplary embodiment, the handles 44a, 44b are slidably disposed within slots 24a, 24b formed between the top and bottom portions 14, 16 of the frame 12. In use, a force can be applied to the handles 44a, 44b such that they slide within the slots 24a, 24b of the frame 12 thereby causing the puller 40 to slide along the tracks 22a, 22b in the sidewall and to move from a first position to a second position to engage a distal portion of the frame 12b and actuate the force-delivery element. While the exemplary embodiment illustrates slidable movement of the puller 40 and driver 30 within the frame 12, a person skilled in the art will appreciate that rotational or any other type of movement can also be used to facilitate movement of the driver 30 and the puller 40 within the frame 12.

As indicated above, the puller 40 is preferably configured to engage the distal end 12b of the frame 12. While the puller 40 can include various features to releasably mate to the frame 12 to hold the puller 40 in an actuated position, in an exemplary embodiment, the puller 40 includes a latch 46 formed therein that mates with an engagement element 18 that is formed on the distal end 16b of the frame 12. FIG. 5C illustrates an exemplary latch 46 that includes two hook-like arms 47a, 47b that extend into corresponding bores in the engagement element 18. The latch 46 can be a push-push latch or a slam latch, such as those made by Southco, or any other type of latch known in the art. In use, and upon distal movement of the puller 40, the latch 46 can be mated to the engagement element 18 to hold the puller 40 in a distal position whereby the force-delivery element is expanded. The latch 46 and engagement element 18 are also preferably releasable. In an exemplary embodiment, the latch 46 can be released from the engagement element 18 by depressing the handles 44a, 44b on the puller 40. A person skilled in the art will appreciate that the mating components on the frame 12 and the puller 40 can be reversed, and the puller 40 can include an engagement element and the frame 12 can include a latch. Various other mating techniques can be used such as threads, or any other type of male and female connector known in the art.

The device can also include features to lessen and/or prevent siphoning of fluid from the syringe when the force-delivery element 50 is in an unactuated or contracted position, and the driver and the puller 40 are located adjacent to one another. In one embodiment, the force-delivery element 50 can be positioned to push against the bottom wall of the frame 12, as shown in FIG. 6, to cause the puller 40 to be forced in an upward position, thereby generating friction between the force-delivery element 50 and the bottom portion 16 of frame 12 and between the puller 40 and the top portion 14 of frame 12. When the force-delivery element 50 is actuated, it will straighten out such that it is not in contact with the frame 12 so that the frame 12 does not interfere with the movement of the driver 30. Additionally or alternatively, the driver 30 can be configured to force the puller 40 towards the frame 12 to generate friction between the puller 40 and the top portion of the frame 12. For example, the driver 30 can include an engagement surface 52 formed on a distal end 30b thereof that contacts a corresponding engagement surface 54 formed on the proximal end 40a of the puller 40 when the driver 30 and puller 40 are positioned adjacent to one another within the frame 12. While the engagement surfaces 52, 54 can have a variety of configurations, as shown in FIGS. 4 and 5B respectively, they can be corresponding slopes or ramped surfaces that abut against one another. In an exemplary embodiment, the engagement surfaces 52, 54 can have an angle in the range of about 25-45 degrees from the direction of travel. In use, the engagement surfaces 52, 54 can be wedged against one another to cause the puller 40 to be pushed upward against the top portion 14 of the frame 12 and thereby help retain the driver 30 and puller 40 in the initial resting position. In other embodiments, the rails or tracks 22a, 22b located in the frame 12 for slidably receiving the puller 40 can include bumps or detents formed thereon to prevent accidental movement of the puller 40 and the driver 30 within the frame 12.

Figure 9A:
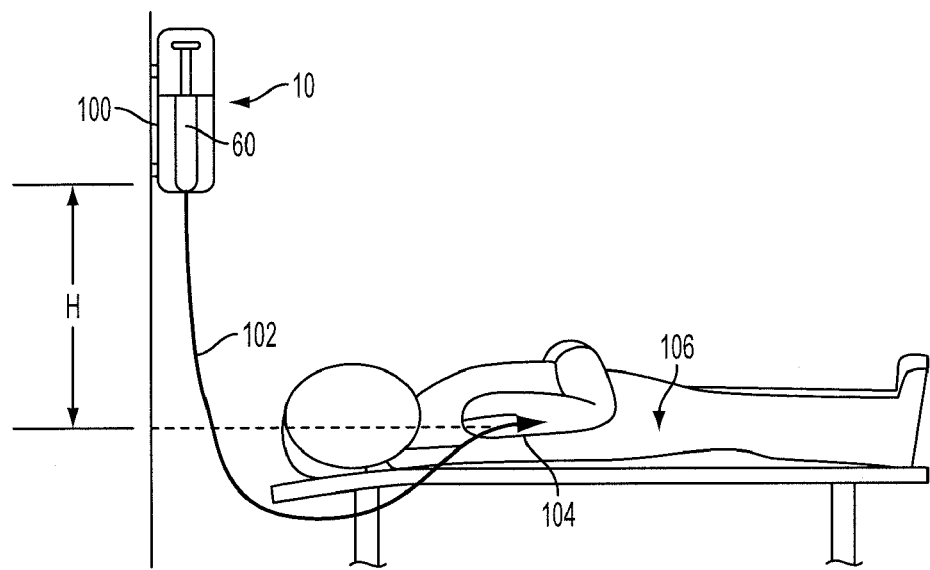
FIG. 9A is a schematic of one embodiment of the system of FIG. 1 in use.

FIGS. 9A-9D further illustrate the various anti-siphoning features of the device 10 discussed above and exemplary method for determining the forces necessary for preventing siphoning. FIG. 9A illustrates the system in use, showing the syringe driver 10 attached to a typical pole or stand 100. A syringe 60 is attached to the driver 10, and an IV line 102 extends from the syringe 60 and includes an IV needle 104 that is inserted into the patient 106. As shown, the syringe driver 10 is at a level higher than the insertion point of the IV needle 104. This height difference H creates a negative pressure within the syringe 60. In this condition it would be possible for the negative pressure in the syringe 60 to pull the syringe plunger downward so that fluid begins to flow unintentionally, possibly causing a danger to the patient 106.

Generally, the negative pressure that occurs can be calculated using the following formula:

$$P = D*H,$$

where P is the pressure, D is the fluid density, and H is the height difference as shown below. For water and most aqueous solutions the density is approximately 0.04 lb/in³. Thus, for example, a 36 inch (3 foot) height difference will produce a negative pressure of approximately 1.4 psi. Typical syringes require about 1 to 3 psi of pressure to overcome static friction and initiate motion of the plunger, however this varies by manufacturer and syringe size. While unwanted flow due to negative pressure will not always occur, it is likely unless anti-siphoning features are provided. Generally, the cross-sectional area of the plunger for a 10 cc syringe has a maximum value of about 0.3 square inches, and the force exerted by a 3 psi pressure is therefore about 0.9 pounds. If the anti-siphoning mechanism applies a friction load greater than this, flow due to any height difference will be prevented.

In one embodiment, the friction load applied by the anti-siphon mechanisms can be estimated as follows, as will be discussed in more detail below. The applied friction load is not a force itself but rather a measure of the force that must be applied to produce movement. The friction load can be calculated using the following formula:

$$F_f = C_f * F_n,$$

where $F_n$ is the force normal to surface, $F_f$ is the applied friction load, and $C_f$ is the coefficient of static friction, which is dependent on the specific materials employed.

Figure 9B:
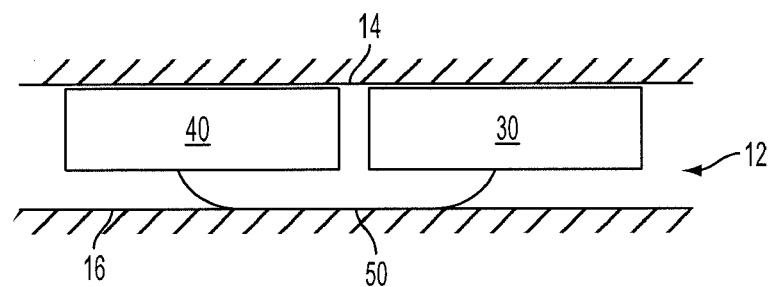
FIG. 9B is a schematic of an anti-siphoning feature of the system of FIG. 1.

As noted above, at least two anti-siphoning features have been described for the present invention, the first of which employs a normal force generated directly by the force delivery element and the second of which employs an engagement surface between the puller and driver. FIG. 9B illustrates the normal force that is generated directly by the force delivery element 50. As shown, the force delivery element 50 is positioned so that the extended section presses against the bottom portion 16 of the frame 12. This side load on the force delivery element 50, acting normal to the bottom portion 16, can vary depending upon the exact geometry of the frame 12 and on the manufacturing process used to create the force delivery element 50, however the normal load can be about one-fourth of the force delivery element tension force. By way of non-limiting example, if the nominal force delivery element tension is about 3.25 pounds, the normal force will be about 0.8 pounds.

A person skilled in the art will appreciate that the coefficient of friction between the metallic force delivery element 50 and the polymeric bottom portion 16 will depend on the properties of the materials. For a metallic to polymeric interface, the coefficient of friction is typically about 0.2. As shown, the reaction force at the ends of the force delivery element 50 is divided approximately equally between the puller 40 and driver 30, causing the puller 40 to be forced against the top portion 14 of the frame 12 with one-half of the normal force of the force delivery element 50. The coefficient of friction between the two polymeric surfaces (that is, the puller 40 and the top portion 14 of the frame 12) will also depend on surface roughness and material type. For ABS (Acrylonitrile Butadiene Styrene) type materials, the coefficient of friction is in the range of about 0.4. The overall friction load is thus:

$$F_f = C_{f1}*F_n + C_{f2}*F_n/2 = 0.2*0.08 + 0.04*0.08/2 = 0.32 \text{ pounds,}$$

where $C_{f1}$ is the coefficient of static friction between metallic and polymeric surfaces, and $C_{f2}$ is the coefficient of static friction between two polymeric surfaces.

Figure 9C:
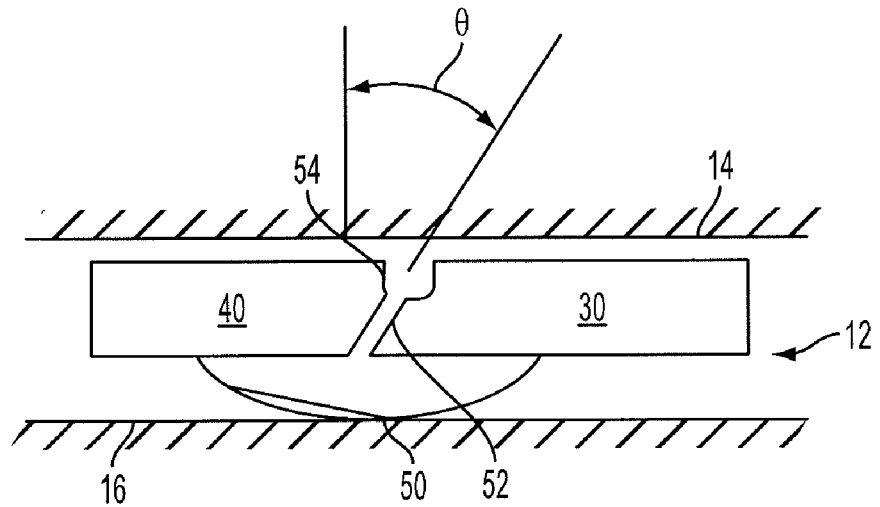
FIG. 9C is a schematic of another anti-siphoning feature of the system of FIG. 1.

FIG. 9C illustrates the normal force provided by engagement surfaces 52, 54 formed on the puller and driver 40, 30. As shown, the engagement surfaces 52, 54 press the puller 40 against the top portion 12 of the frame 12 when the force delivery element 50 pulls the puller and driver 40, 30 into contact with each other. As a result, the normal force created can be calculated using the following formula:

$$F_f = F_s * \tan(\theta),$$

where θ is the contact angle. For a contact angle of 35 degrees, for example, the friction load is then given by:

$$F_f = C_{f2} * F_s * \tan(\theta) = 0.4 * 3.25 * \tan(35) = 0.91 \text{ pounds}.$$

The two friction loads, as shown in the above examples can be added together for a combined total of 1.23 pounds, which is well in excess of the required holding force and can therefore prevent the occurrence of any siphoning.

Figure 9D:
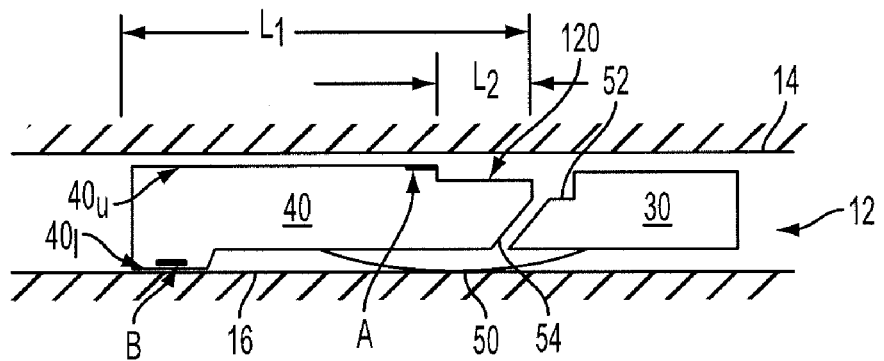
FIG. 9D is a schematic of another anti-siphoning feature of the system of FIG. 1.

If greater holding force is required, or if low-friction plastics are employed, the normal forces between the puller 40 and the frame 12 can be further increased by a simple geometric modification, as shown in FIG. 9D. As shown, the puller 40 has an overall length $L_1$. The upper surface 40*u* of the puller 40 is relieved by a relief slit 120 so that there is no contact between the puller 40 and the top portion 14 of the frame 12 for a length $L_2$ adjacent to the engagement surface 52 with the driver 30. This creates a lever arm that magnifies the normal forces. Most of the contact force will occur along small areas A and B on the upper and lower surfaces 40*u*, 40*l* of the puller 40, respectively. At A the resulting friction load can be calculated using the following formula:

$$F_{fA} = \frac{L_1}{L_1 - L_2} * C_{f2} * F_s * \tan(\theta).$$

At B the friction load can be calculated using the following formula:

$$F_{fB} = \frac{L_2}{L_1 - L_2} * C_{f2} * F_s * \tan(\theta).$$

Thus, the total friction load is increased by $L_1 + L_2/L_1 - L_2$. If, for example, the puller 40 is relieved for ¼ of its length, the friction load is increased by a factor of 1.67. A person skilled in the art will appreciate that the syringe driver of the present invention can have a variety of other modifications to create a greater holding force and prevent anti-siphoning.

FIG. 7 illustrates one embodiment of a syringe 60 for use with the device 10. As shown, the syringe 60 is a standard syringe having a plunger 62 with a flange 63 formed on the proximal end thereof, and a barrel 64 that receives the plunger 62 and retains fluid therein. As previously explained, a luer fitting is used to mate the syringe to the frame. This allows the device to work with any size syringe. While a variety of luer fittings can be used, the luer fitting 66 can include a female fitting 70 on one end and a male fitting 72 on the opposite end. The female fitting 70 has a substantially cylindrical opening and can mate with the distal end 60*b* of the syringe 60. The male fitting 72 is adapted to mate with the connecting element of the frame 12, and thus has a collar portion or barrel for receiving the protrusion 29. A fluid conduit, such as tubing, for fluid delivery can also extend from the male fitting 72. In use, the collar of the luer fitting can be placed within the cavity 28 of the connecting element and the underside of the collar can be engaged by the protrusion 29 such that the luer fitting 66 is securely held within the frame 12. While the luer fitting 66 can be coupled to any size syringe, in an exemplary embodiment the syringe 60 has a volume in the range of about 5-60 cc, and more preferably about 10-60 cc.

Figure 10:
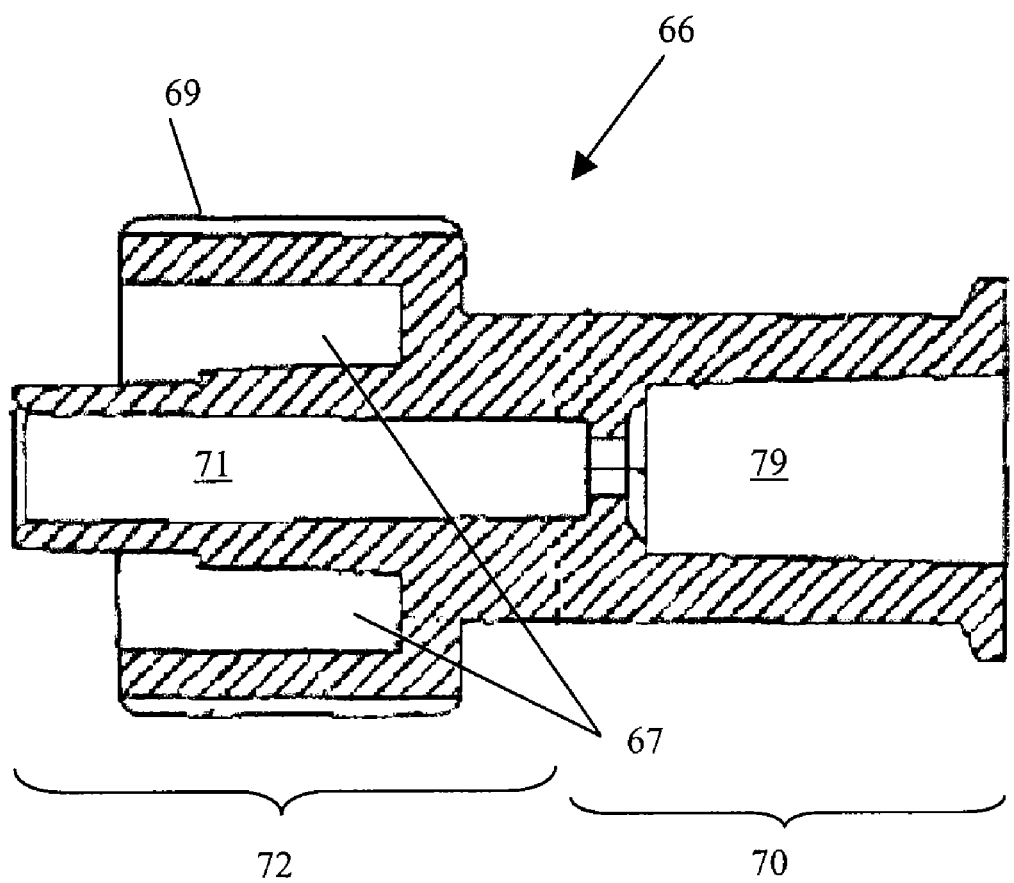
FIG. 10 is a cross-section view of one exemplary luer fitting for use with the system of FIG. 1.

FIG. 10 shows an exemplary embodiment of a luer fitting 66 for use with the syringe driver of the present invention. The luer fitting 66 is similar to a standard luer, and it includes a female fitting 70 having a socket 79 that is adapted to mate to a barrel of a syringe, and a male fitting 72 for receiving a fluid conduit, such as tubing. As shown, the male fitting 72 has a collar 69 that surrounds a nozzle 71, and a socket 67 formed between the collar 69 and the nozzle 71. The socket 67 of the male fitting 72, however, is non-threaded to allow the protrusion to be received therein without threading the luer fitting 66 into the connecting element. The additional benefit of the exemplary luer fitting 66 is that standard luer fittings, which have threads on the socket and/or collar walls, cannot mate to the device 10. This ensures that incorrect fluid conduits or luer fittings 66 will not be used with the device 10. The fluid conduit can be mated to the luer fitting 66 using a variety of techniques. For example, the fluid conduit can be secured to the nozzle 71 of the luer fitting 66 using an adhesive, such as glue.

Figure 8A:
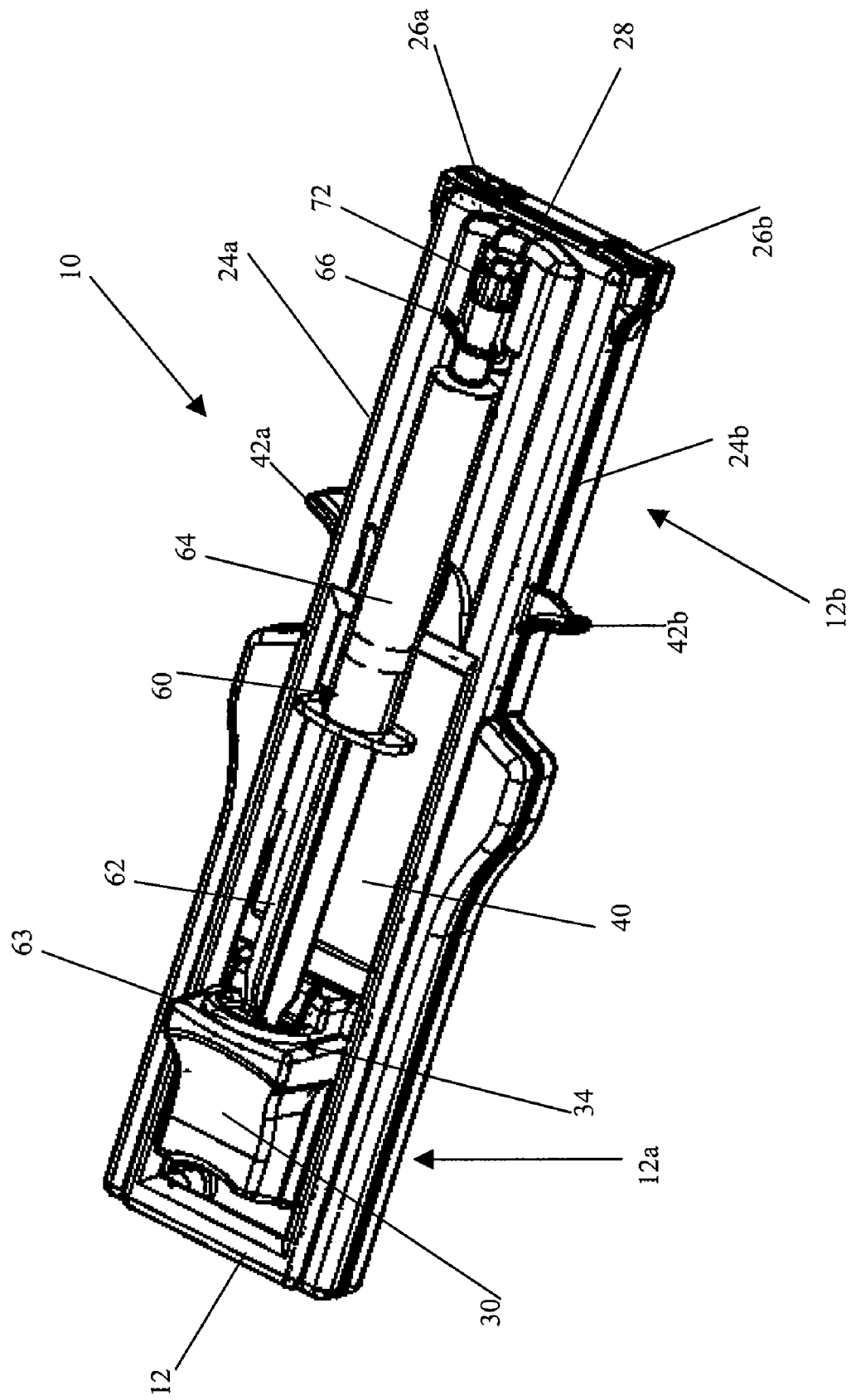
FIG. 8A is a perspective view of the system of FIG. 1 in use, showing the driver and the puller in an initial position.
Figure 8B:
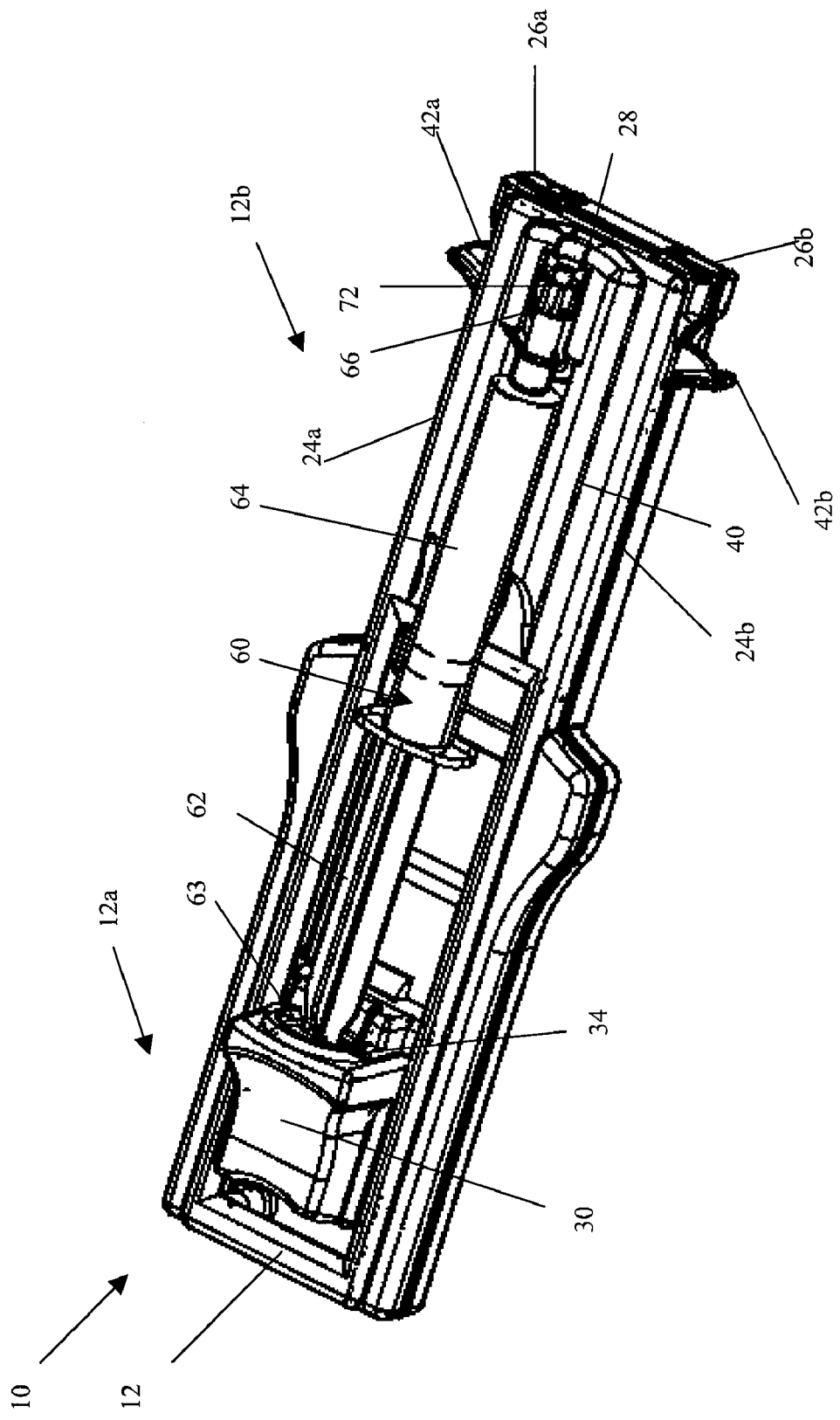
FIG. 8B is a perspective view of the system of FIG. 8A, showing the puller engaged with the distal portion of the frame.
Figure 8C:
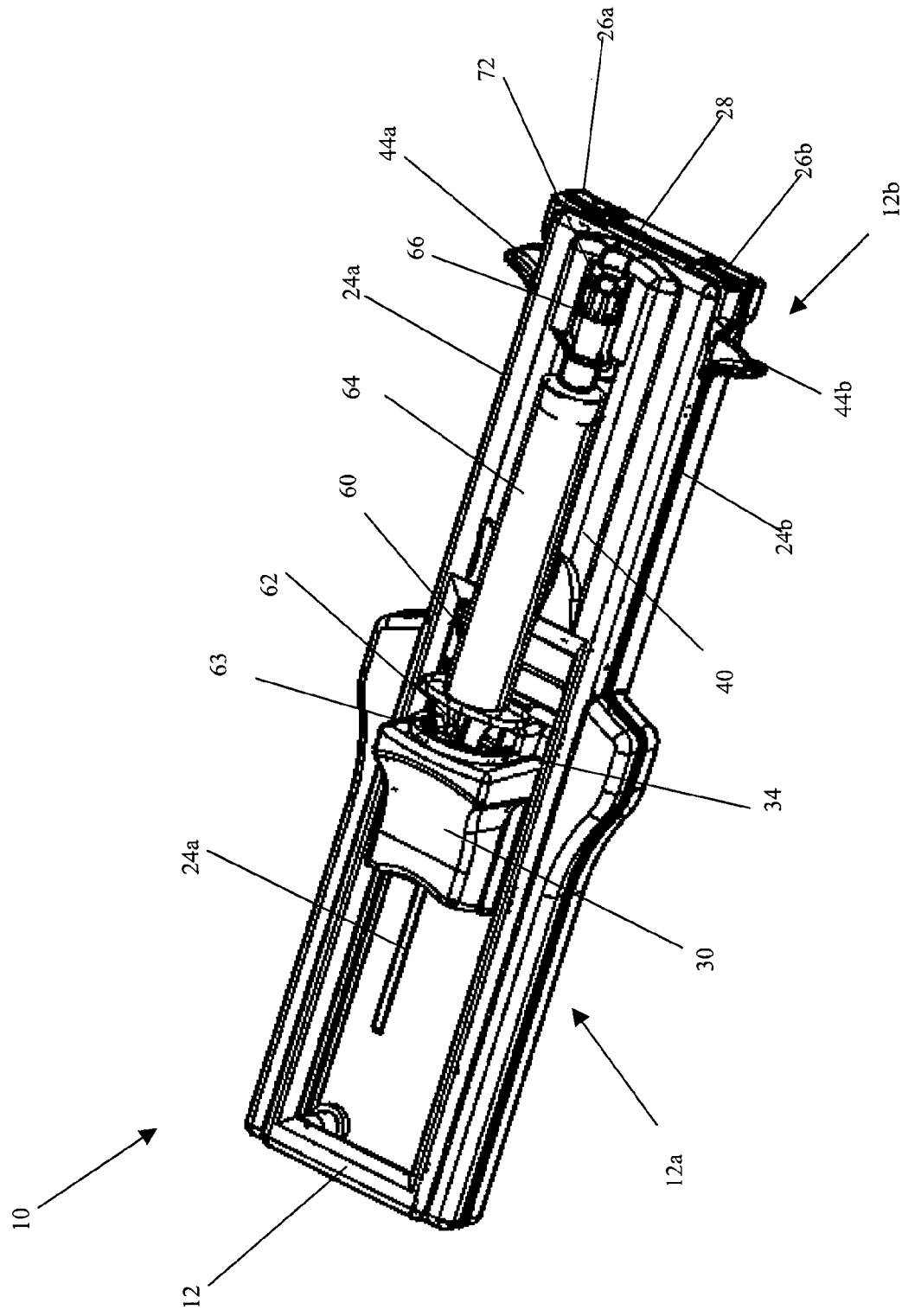
FIG. 8C is a perspective view of the system of FIG. 8B, showing the driver moved in a distal direction to advance a plunger into a barrel of the syringe.

FIGS. 8A-8C illustrate one exemplary method for driving fluid from a syringe using the system of FIGS. 1-7. Referring first to FIG. 8A, the driver 30 and the puller 40 can be slid to the proximal end of the frame 12*a* such that they are in contact with one another to create sufficient space within the frame 12 for receiving the syringe 60. The female fitting 70 of the luer fitting 66 can be placed on the distal end of the syringe 60 to prepare the syringe 60 for mating with the frame 12. The syringe 60 can then be positioned within the frame 12 by mating the luer fitting 66 to the connecting element located on the top portion 14 of the frame 12. Preferably, the male fitting 72 is engaged by the protrusion of the connecting element such that luer fitting 66 sits within the cavity 28 and the fluid conduit (not shown) is positioned within and extends outwardly from the cut-out of the protrusion. The plunger 62 of the syringe 60, and preferably the flange 63 formed thereon, can then be engaged by the cavity 34 on the driver 30, and the barrel 64 of the syringe 60 can be positioned within the cavity 17 of the frame. Where the syringe plunger is cut off or is short, a prosthetic plunger (not shown) can be mated to the shortened plunger, so that it can be engaged by the driver 30. The prosthetic plunger can be attached to the device 10 by a flexible cord, chain, or other component to prevent loss of the prosthetic plunger when it is not in use.

Once the syringe 60 is positioned within the frame 12, the force-delivery element can be actuated to move from a contracted position to an expanded position to apply force to the driver 30, and thereby cause the plunger 62 to move into the barrel 64 of the syringe 60. As noted above, the puller 40 can be used to actuate the force-delivery element. As shown in FIG. 8B, the puller 40 can be slid within the frame 12 from a first position where the puller 40 is substantially adjacent to the driver 30 to a second position where the puller 40 is positioned at the distal end 12*b* of the frame 12. This movement can be achieved by a two-handed technique where a user can optionally position their thumbs on the protrusions 26*a*, 26*b* on the distal end of the frame 12*b* and their fingers on the handles 44*a*, 44*b* of the puller 40 to apply a force to the handles 44*a*, 44*b* to thereby slide the handles 44*a*, 44*b* within the slots 24*a*, 24*b* of the frame 12. Once at the distal end 12*b* of the frame 12, the latch located on the puller 40 can engage and mate to the engagement element on the frame 12.

As the puller 40 moves from the first position to the second position, the force-delivery element is moved from a contracted position, where it is wound on the hub of the driver 30, to an expanded position. Once the puller 40 is mated to the distal end of the frame 12, the force-delivery element is held in the expanded position, and will begin to recoil within the hub of the driver 30 to return to its contracted position. As shown in FIG. 8C, the recoiling of the force-delivery element causes a force to be applied to the driver 30 such that the driver 30 slides along the tracks (track 24*a* is shown) in a distal direction towards the puller 40 and the distal end 12b of the frame 12. The driver 30 thus forces the plunger 62 into the barrel 64 of the syringe 60, thereby causing fluid to flow from the syringe 60 and into the fluid conduit extending therefrom to be delivered to the patient. Once fluid delivery is complete and the force-delivery element returns to its contracted position, the latch and the engagement element can be disengaged by depressing the handles 44a, 44b on the puller 40. As a result, the driver 30 and the puller 40 can be moved towards the proximal end of the frame 12a to allow the syringe 60 to be removed and a new syringe to be added.

In other embodiments, the syringe drivers disclosed herein can be reconditioned for reuse after at least one use. Reconditioning can include any combination of the steps of disassembly of the device, followed by cleaning or replacement of particular pieces, and subsequent reassembly. By way of example and in the event that the connecting element and/or the luer fitting breaks or otherwise needs to be replaced, it can be removed from the device and selectively replaced. Upon replacement, the device can be reassembled for subsequent use. Those skilled in the art will appreciate that reconditioning of a syringe driver device can utilize a variety of techniques for disassembly, cleaning/replacement, and reassembly. Use of such techniques, and the resulting reconditioned syringe driver device, are all within the scope of the present application.

A person skilled in the art will appreciate that the present invention can be made of any material that is durable such that the device can be reusable as well as able to withstand being dropped from at least 1.5 m onto a hard surface (such as a floor). Exemplary materials include plastics and metals. A person skilled in the art will further appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A syringe driver, comprising:
a frame adapted to seat a syringe;
a driver slidably disposed within the frame and adapted to seat a plunger of a syringe;
a puller slidably disposed within the frame and having a latch formed thereon and adapted to
mate to an engagement element on the frame; and
a force-delivery element coupled to and extending between the driver and the puller, the force-delivering element mating to the driver at a location adjacent to a proximal end of a plunger of the syringe, the force delivery element pressing against the frame to create a frictional force between the puller and the frame sufficient to prevent siphoning of the syringe;
wherein the puller is movable between a first position, in which the force-delivery element is in a resting position, and a second position, in which the latch on the puller mates to the engagement element on the frame to expand the force-delivery element thereby causing the force-delivery element to pull the driver and drive the plunger into a barrel of a syringe seated within the frame.

2. The device of claim 1, wherein the driver is slidably disposed within a proximal portion of the frame, and the puller is slidably disposed within a distal portion of the frame.

3. The device of claim 2, wherein the latch is formed on a distal end of the puller, and the engagement element is formed on a distal end of the frame.

4. The device of claim 3, wherein the puller includes at least one handle formed thereon for slidably moving the puller to mate the latch to the engagement element.

5. The device of claim 4, wherein the latch and engagement element are releasably matable, and wherein depression of the at least one handle is adapted to release the latch from the engagement element.

6. The device of claim 4, wherein the at least one handle comprises opposed handles extending from opposed sides of the puller and through opposed slots formed in the frame.

7. The device of claim 2, wherein the frame includes rails formed thereon for slidably retaining the driver within the frame.

8. The device of claim 2, wherein the frame includes a housing that at least partially surrounds the puller to retain the puller within the frame.

9. The device of claim 8, wherein the force-delivery element is adapted to force the puller into contact with the housing to generate friction between the puller and the housing when the puller is in the first position.

10. The device of claim 9, wherein the driver includes a first engagement surface formed thereon and the puller includes a second, complementary engagement surface formed thereon, the force-delivery element being adapted to cause the first engagement surface on the driver to act against the second engagement surface on the puller to force the puller into contact with the housing to generate a friction between the housing and the puller when the puller is in the first position.

11. The device of claim 10, wherein the first and second engagement surfaces are complementary ramp elements.

12. The device of claim 1, wherein the driver includes a cavity formed therein and adapted to capture a flange formed on a proximal end of a plunger of a syringe.

13. The device of claim 1, wherein the force-delivery element comprises a constant force spring having a portion wound around and mated to a hub formed within the driver.

14. The device of claim 1, further comprising a connecting element formed on a distal end of the frame adapted to connect a syringe to the frame.

15. The device of claim 14, wherein the connecting element comprises a protrusion that is adapted to extend into at least a portion of a luer fitting for mating to a distal end of a barrel of syringe and to couple the syringe to a fluid conduit.

16. The device of claim 15, further comprising a detachable luer fitting at least partially disposed within the connecting element.

17. The device of claim 16, further comprising a fluid conduit that is mated to the luer fitting.

18. The driver of claim 1, wherein the device is adapted to interchangeably receive a plurality of syringes having different sizes.

19. The device of claim 1, wherein a frictional resistance force is created between the puller and the frame.

20. The device of claim 19, wherein at least one of the driver and the force-delivery element are configured to press the puller against the frame to create the frictional resistance force.

21. The device of claim 1, wherein the driver includes a mating element configured to engage and retain a proximal end of the plunger.

22. The device of claim 1, wherein the frame includes a ridge is configured to prevent movement of a barrel of a syringe.

23. A system for driving fluid, comprising: a syringe comprising a barrel and a plunger slidably disposed in the barrel;

a frame having proximal and distal ends, the distal end of the frame being adapted to couple to a distal end of the barrel of the syringe;

a driver slidably disposed within the frame and having a cavity formed therein that retains a proximal end of the plunger for preventing movement of the plunger independently of the driver; and a puller slidably disposed within the frame and movable between a first position, in which a proximal end of the puller is positioned adjacent to the driver and the proximal end of the plunger and a force is applied to the puller by the driver to prevent siphoning of the syringe, and a second position, in which the puller is coupled to a distal end of the frame and a force is applied to the driver to move the driver distally and thereby force the plunger into the barrel of the syringe.

24. The system of claim 23, further comprising a force-delivery element extending between the puller and the driver, and wherein the force-delivery element is in a resting position when the puller is in the first position, and the force-delivery element is actuated to apply a force to the driver when the puller is in the second position.

25. The system of claim 23, wherein the puller has a latch formed thereon adapted to mate to an engagement element formed on the frame.

26. The system of claim 25, further comprising handle portions located on the puller adapted to facilitate releasable engagement of the latch with the engagement element.

27. The system of claim 23, further comprising a connecting element formed on the distal end of the frame adapted to couple the barrel of the syringe to the frame.

28. The system of claim 27, wherein the syringe includes a luer fitting removably mated to a distal end of the barrel, the luer fitting having a socket formed therein for removably receiving a protrusion formed on the connecting element.

29. The system of claim 28, wherein the socket is non-threaded.

30. The system of claim 28, further comprising a fluid conduit that is mated to the luer fitting.

31. The system of claim 23, wherein a frictional resistance force is created between the puller and the frame.

32. The system of claim 31, wherein at least one of the driver and the force-delivery element are configured to press the puller against the frame to create the frictional resistance force.

33. The system of claim 23, wherein the driver includes a mating element configured to engage and retain a proximal end of the plunger.

34. The system of claim 23, further comprising a connecting element formed on a distal end of the frame configured to connect the syringe to the frame.

35. The system of claim 23, wherein the frame includes a ridge is configured to prevent movement of the barrel of the syringe.

36. A method for driving fluid, comprising:

engaging a syringe between a driver slidably positioned within a frame and a connecting element formed on a distal end of the frame; and sliding the puller toward a distal end of the frame to mate the puller to the frame, the puller actuating the force-delivery element coupled at a first end to the puller and at a second end to the driver at a location adjacent to a proximal end of a plunger of the syringe;

whereby the force-delivery element pulls the driver distally to drive the plunger into a barrel of the syringe and thereby drive fluid out of the syringe, wherein, prior to sliding the puller, a combination of at least two of the force delivery element, the driver, and the puller prevents siphoning of the syringe.

37. The method of claim 36, wherein the puller includes a latch formed thereon that mates to an engagement element formed on a distal end of the frame.

38. The method of claim 37, wherein sliding the puller comprises sliding opposed handles formed on the puller distally within opposed slots formed in the housing.

39. The method of claim 38, further comprising depressing the opposed handles to release the latch from the engagement element.

40. The method of claim 36, wherein the force-delivery element comprises a constant force spring that pulls the driver distally.

41. The method of claim 36, wherein engaging the syringe comprises positioning a flange formed on a proximal end of a plunger of the syringe in a cavity formed in the driver, and positioning a luer fitting coupled to a distal end of the syringe within a protrusion formed on the connecting element.

42. The method of claim 36, wherein the fluid is driven from the barrel of the syringe through a fluid conduit coupled to a distal end of the barrel.

43. The method of claim 36, wherein a frictional resistance force is created between the puller and the frame.

44. The method of claim 36, wherein at least one of the driver and the force-delivery element presses the puller against an inner surface of the frame to create a frictional resistance force.

45. The method of claim 36, wherein the driver includes a mating element that engages and retains a proximal end of the plunger.

46. The method of claim 36, further comprising a connecting element formed on a distal end of the frame that connects the syringe to the frame.

47. The method of claim 36, wherein the frame includes a ridge that prevents movement of the barrel of the syringe.

* * * * *